United States Patent [19]
Chavis

[11] 4,143,191
[45] Mar. 6, 1979

[54] SIMULATED BLOOMING FLOWER ARRANGEMENT

[75] Inventor: Yvonne Chavis, Camden, N.J.

[73] Assignee: Douglas Jefferson, Camden, N.J.

[21] Appl. No.: 781,648

[22] Filed: Mar. 28, 1977

[51] Int. Cl.² ............................................. A01N 3/00
[52] U.S. Cl. ........................................ 428/13; 46/41; 47/41 R; 47/41.12; 47/69; 428/24; 428/35; 428/913
[58] Field of Search ............... 46/41; 428/13, 24, 25, 428/26, 35, 913; 47/48.5, 41, 41.12; 24/5; 206/423

[56] References Cited
U.S. PATENT DOCUMENTS

| 785,055 | 3/1905 | Spicer | 428/24 X |
| 2,777,233 | 1/1957 | Brandhurst | 428/13 X |
| 2,837,855 | 6/1958 | Hoke | 428/24 X |
| 3,471,964 | 10/1969 | Cherry et al. | 428/24 X |
| 3,816,224 | 6/1974 | Smart et al. | 428/13 X |
| 3,998,005 | 12/1976 | Way | 428/16 X |

Primary Examiner—Henry F. Epstein
Attorney, Agent, or Firm—Duffield & Lehrer

[57] ABSTRACT

A flower pot is substantially filled with granular material or soil and is adapted to retain water therein. A clear plastic bubble shaped cover rests on the top ledge of the pot. A plurality of dried flowers are mounted in the granular material and extend upwardly from the pot. The flowers are adapted to close when the cover is on the pot as a result of increased ambient humidity and are adapted to open when the cover is removed as a result of decreased ambient humidity.

4 Claims, 3 Drawing Figures

SIMULATED BLOOMING FLOWER ARRANGEMENT

BACKGROUND AND SUMMARY OF THE INVENTION

The present invention is directed toward a simulated blooming flower arrangement and more particularly to a flower pot and cover arrangement for displaying the same.

Flowers, real, dried and artificial, are widely used for decorative purposes in homes, offices and other buildings. While dried and artificial flower arrangements are normally very attractive, many people do not like them because of their lack of growth and change. In other words, they always look the same. For this reason, many people prefer live flowers and plants. However, live flowers and plants are difficult to take care of and will die if proper care is not taken. In addition, live flowers and plants will only grow if conditions, such as adequate sunlight, are right.

The present invention has advantages of both artificial and live flower and plant arrangements. It presents an arrangement which is both pleasing and requires no care but which can exhibit characteristics of live blooming flowers. The invention is comprised of a flower pot which is substantially filled with granular material or soil and is adapted to retain water therein. A clear plastic bubble shaped cover rests on the top ledge of the pot. A plurality of dried flowers are mounted in the granular material and extend upwardly from the pot. The flowers are adapted to close when the cover is on the pot as a result of increased ambient humidity and adapted to open when the cover is removed as a result of decreased ambient humidity. Thus, the invention not only provides a decorative and ornamental arrangement but is also educational since it demonstrates the manner in which the petals of a flower open and close.

DESCRIPTION OF THE DRAWINGS

For the purpose of illustrating the present invention, there is shown in the accompanying drawings one form which is presently preferred; it being understood that the invention is not intended to be limited to the precise arrangements and instrumentalities shown.

DETAILED DESCRIPTION OF THE PREFERRED EMBODIMENT

Figure 1:
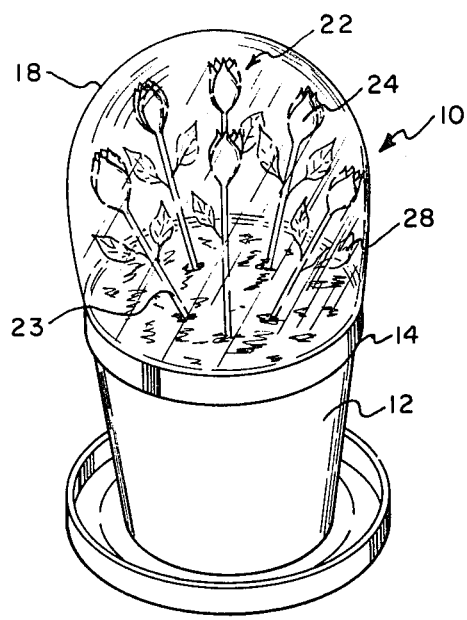
FIG. 1 is a perspective view of a simulated blooming flower arrangement constructed in accordance with the principles of the present invention.

Referring now to the drawings in detail, wherein similar reference numerals have been used throughout the various figures to designate similar elements, there is shown in FIG. 1 a simulated blooming flower arrangement constructed in accordance with the principles of the present invention and designated generally as 10.

The arrangement 10 includes a flower pot 12 of substantially conventional configuration and having an upper flange 14. The pot 12 is preferably made of a nonporous material such as plastic, glazed porcelain or the like so that it can retain water therein. The pot 12 is filled with a granular material 16 such as sand, gravel or the like which is capable of supporting a substantially rigid rod therein such as the stem of a flower. Other materials, such as soil, foamed plastics or the like may be used in place of the granular material 16. The only requirement being that the material be capable of allowing a flower stem to pass there through and support the same.

As shown in FIG. 1, a clear transparent plastic or glass bubble cover 18 is adapted to fit over the top of flower pot 12. The cover 18 has an annular flange 20 adjacent the lower part thereof which flange is adapted to cooperate with flange 14 of the pot 12. While it is not necessary that the flanges 14 and 20 cooperate to form a perfect airtight seal there between, it is preferable to have a relatively close tolerance between the two seals to prevent substantial passage of air there between.

Figure 2:
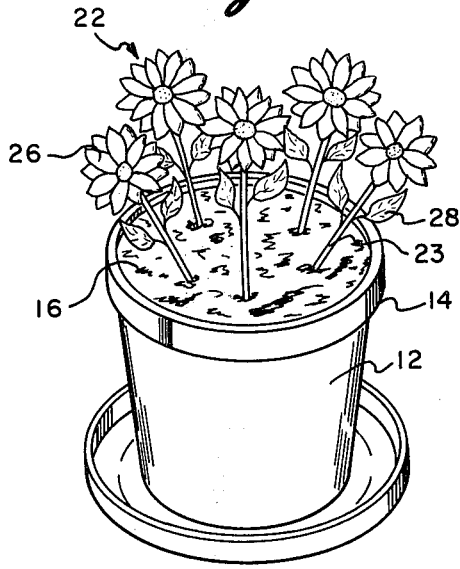
FIG. 2 is a view similar to FIG. 1 but with the cover removed and showing the petals of the flowers open.
Figure 3:
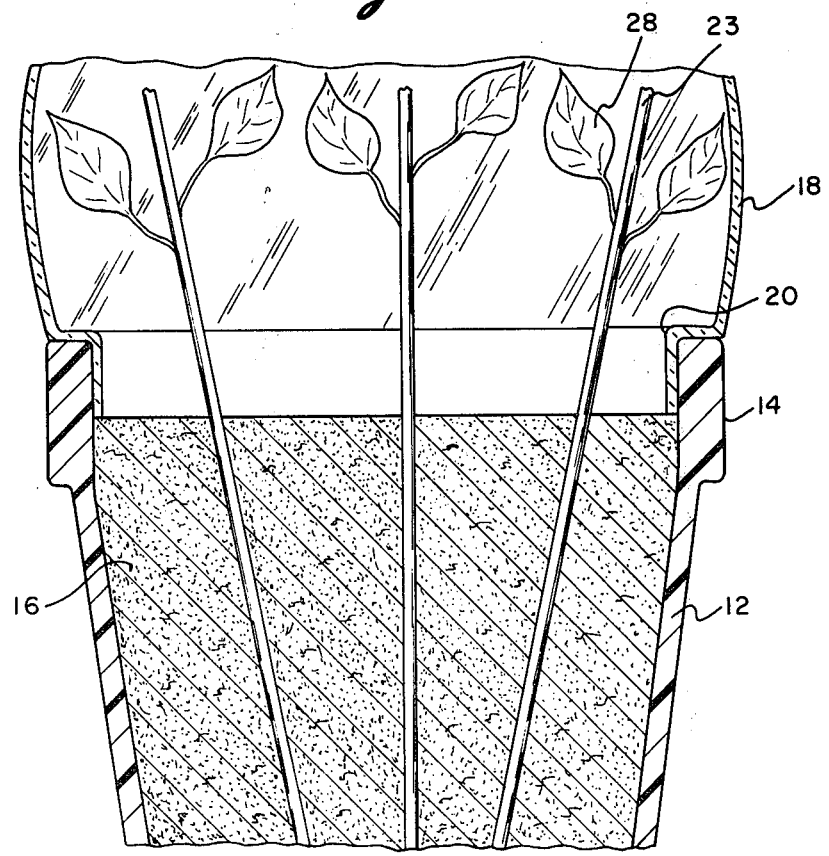
FIG. 3 is an exploded cross-sectional view taken along the line 3—3 of FIG. 1.

Positioned within the pot 12 and supported by the granular material 16 are a plurality of flowers 22. The flowers are supported by their stems 23 in the granular material 16. In the preferred embodiment, flowers 22 are dried starflowers. The petals of these dried starflowers are relatively sensitive to humidity. When the ambient humidity is relatively high, the petals tend to close up as shown in FIG. 1 to give the appearance of a bud 24. However, when the ambient humidity is relatively low, the petals gradually open to give the appearance of a fully blossomed flower 26 as shown in FIG. 2.

While dried starflowers are employed in the preferred embodiment of the present invention, it should be readily apparent that artificial and other dried flowers may also be employed; the only requirement being that the petals of the flowers curl toward a closed position when the ambient humidity is high as a result of the cover being in place and curl to an open position when the ambient humidity is relatively low when the cover is removed. In addition to the flowers in the pot 12, other decorative materials such as greens may be used to decorate the arrangement. The leaves 28 on the stems may be the original real leaves of the flowers or artificial leaves which are attached to the stems.

The above described invention is used in the following manner. With transparent plastic cover 18 removed from the pot 12, a quantity of water is poured into the pot through the granular material 16. When the cover 18 is placed over the pot 12, the atmosphere within the cover 18 eventually becomes humid as a result of the water within the pot 12. As a result, the petals of the flowers being to close to give the appearance of buds as shown in FIG. 1. This occurs at a relatively moderate rate so that one can actually watch the petals close.

Thereafter, the cover 18 may be removed from the pot 12. When this occurs, the humidity which had built up around the flowers and within the cover 18 moves away therefrom and eventually the atmosphere has a relatively low humidity.

As a result of the relatively low ambient humidity in the vicinity of the flowers 22, the petals begin to uncurl and open giving the appearance of a fully blossomed flower 26 as shown in FIG. 2. This also occurs at a relatively moderate rate so that one can watch the petals open. Thus, it should be readily apparent that the present invention can also be used as an educational device to demonstrate the manner in which petals of a flower open and close.

The present invention may be embodied in other specific forms without departing from the spirit or essential attributes thereof and, accordingly, reference should be made to the appended claims, rather than to the foregoing specification as indicating the scope of the invention.

I claim:

1. A simulated blooming flower arrangement comprising:
   a flower pot including material therein capable of supporting a substantially rigid stem of a flower, said pot and material further being adapted to retain water therein;
   a plurality of flowers having elongated rigid stems, said stems being held by said material within said pot so that the petals of said flowers are located above the top of said pot;
   the petals of said flowers being adapted to close to give the appearance of a bud when in the presence of humidity and being adapted to open to give the appearance of a fully blossomed flower in the absence of humidity;
   a substantially transparent imperforate cover member, and
   means on said cover member cooperating with means on said pot to enable said cover member to temporarily rest on the top of said pot and around said flowers whereby said cover member can be readily removed from and applied to said pot.

2. A simulated blooming flower arrangement as claimed in claim 1 wherein said transparent cover member is substantially bubble shaped.

3. A simulated blooming flower arrangement as claimed in claim 1 wherein said flowers are dried starflowers.

4. A simulated blooming flower arrangement as claimed in claim 1 wherein said material is granular.